United States Patent [19]

Moore

[11] Patent Number: Plant 7,061

[45] Date of Patent: Dec. 5, 1989

[54] ROSE PLANT/MORCHERMAG

[75] Inventor: Ralph S. Moore, Visalia, Calif.

[73] Assignee: Sequoia Nursery, Visalia, Calif.

[21] Appl. No.: 252,905

[22] Filed: Oct. 3, 1988

[51] Int. Cl.[4] ..... A01H 5/00

[52] U.S. Cl. ..... Plt./10

[58] Field of Search ..... Plt. 10

*Primary Examiner*—James R. Feyrer

[57] ABSTRACT

The subject of the present disclosure is a new and distinct variety of miniature rose plant characterized by red buds and flowers of good substance and keeping qualities.

1 Drawing Sheet

The present invention relates to a new and distinct variety of hardy, dwarf bush type rose plant of the miniature class: the variety being primarily characterized — as to novelty — by small red buds and flowers. The general color effect being medium to dark red.

The variety is further characterized by:

An abundance of bloom, with flowers, on mature plant, borne both singly and several together in loose spray or cluster.

Little or no fragrance.

A plant which is vigorous, of rounded, somewhat upright shape with semi-glossy to matt, small foliage with pointed leaflets; the buds and flowers being similar in form to Lavender Jewel (miniature — U.S. Plant Pat. No. 4,480) but smaller.

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif. under conditions of careful control and observation, as a cross between Anytime (miniature — not patented) as the seed parent and Lavender Jewel (Minature — U.S. Plant Pat. No. 4,480) as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; upright; seedling; greenhouse; outdoors; cut flowers; garden decoration.

Class: miniature.

*International identification.*—Variety: Morchermag.

*Commercial synonym.*—Cherry Magic.

Flowers borne: sometimes singly but more often in loose cluster or spray of 3 to 5 or more on slender wirey stems.

Quantity of bloom: Abundant both outside and in greenhouse.

Bud:

*Peduncle.*—Short to medium; slender but sturdy; erect; medium green, sometimes lightly tinted bronze (outdoors).

*Hairs.*—Numerous very fine short hairs. Before calyx breaks; size — small. Form; pointed with several small foliaceous apendages and few (or no) small hairs on surface of bud; with foliaceous parts extending beyond the tip of the bud equal to one-half or less of its length.

*Color.*—Medium green, occasionally tinted with bronze (outdoors). As calyx breaks, color — medium to dark red. Opening: opens well in all weather.

Bloom:

*Size when fully open.*—Small, averaging about 30 mm (1¼").

*Petalage.*—Double — averaging about 25 petals arranged regularly plus sometimes several small petaloids.

*Form.*—High centered then becoming more flat to rounded with petals reflexing loosely outward, and later at maturity, rolled loosely outward and downward. Open flowers may show stamens.

Petals: Fairly thick; velvety on inside and satiny on outside surface.

*Shape.*—Outside petals, broad lanceolate (almost round); rounded tip; intermediate — broad lanceolate (almost round) with very short acute tip; inside — broad lanceolate with or without acute tip.

Color: Newly opened flower from a plant grown in plastic greenhouse (September 1988), Visalia, Calif.

*Outside petal.*—Outside surface — near Chrysanthemum Crimsom 824/2 or lighter, and veined or underlaid lighter with small near white area at petal base. Inside surface — near, but not as dark as Chrysanthemum Crimsom 824/1 and darker than Current Red 821, with small near white area at petal base.

Note: There is no matching color on this Chart, but above color description gives an overall idea as to color. The red color is deepened by blackish shading or veins but flower appears brighter than colors as set forth above.

*Intermediate petal.*—Outside surface similar to outside petal. Inside surface — similar to outside petal.

*Inner petal.*—Outside surface — similar to intermedate petal. Inside surface — similar to intermediate petal. General color effect; newly opened flowers — deep red. Three days open — color similar. Behavior — opens well in all weather. Spent petals drop off. Flower longevity (September 1988) — plant in pot 5–7 days or longer. Cut flowers at living room temperature 4–6 days or longer.

Reproductive organs:

*Stamens.*—Several, arranged regularly about pistils.

*Filaments.*—Varying length, fairly short, light yellow.

*Anthers.*—Yellow.

*Pollen.*—Moderate amount.

*Pistils.*—Average number.

*Styles.*—Fairly even; short length; bunched; color — light reddish.

*Ovaries.*—All enclosed in calyx.

*Hips.*—Some, ball shaped, orange.

*Sepals.*—Permanent; spear shape; recurved against peduncle.

*Seed.*—Few to several.

Foliage:

*Leaves.*—Compound of five (sometimes three or seven) leaflets; fairly small; leathery; semi-glossy to matt.

*Leaflets.*—Shape: broad, lanceolate; apex acute; base rounded. Margin serrate. Color: medium to dark green; new growth — normal (medium) green — sometimes reddish (outdoors). Rachis: medium strength; upperside may have a few very tiny short hairs, grooved; underside sparsely thorny (very small) with few or no tiny prickles or hairs. Stipules: medium length; narrow to medium width; short length; narrow points which turn out usually at about 45 degrees or less.

Growth:

*Habit.*—Dwarf; bushy; rounded to upright; much branched.

*Growth.*—Free vigorous; internodes short.

*Canes.*—Medium slender; sturdy.

*Main stems.*—Color: medium green.

*Thorns.*—Few to moderate amount. Prickles — none.

*Branches.*—Color: medium green. Thorns: few. Note: Growth buds (in axil of each leaf) are more plump than average thus making budding easier (and more successful) which is an advantage in producing miniature tree rose plants.

*Prickles.*—None. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of minature rose plant of hardy, dwarf, bushy, rounded to upright, much branched habit, substantially as illustrated and described, characterized by buds and flowers of medium to deep red color which is modified by lighter red veining or undercolor; the bud and flower resembling the variety Lavender Jewel (U.S. Plant Pat. No. 4,480) in form and further characterized by a plant of vigorous and compact growth habit, easy to propagate from cuttings or by budding, with an abundance of small to medium size semi-glossy to matt foliage and an abundance of flowers borne both singly and in loose clusters of 3 to 5 or more.

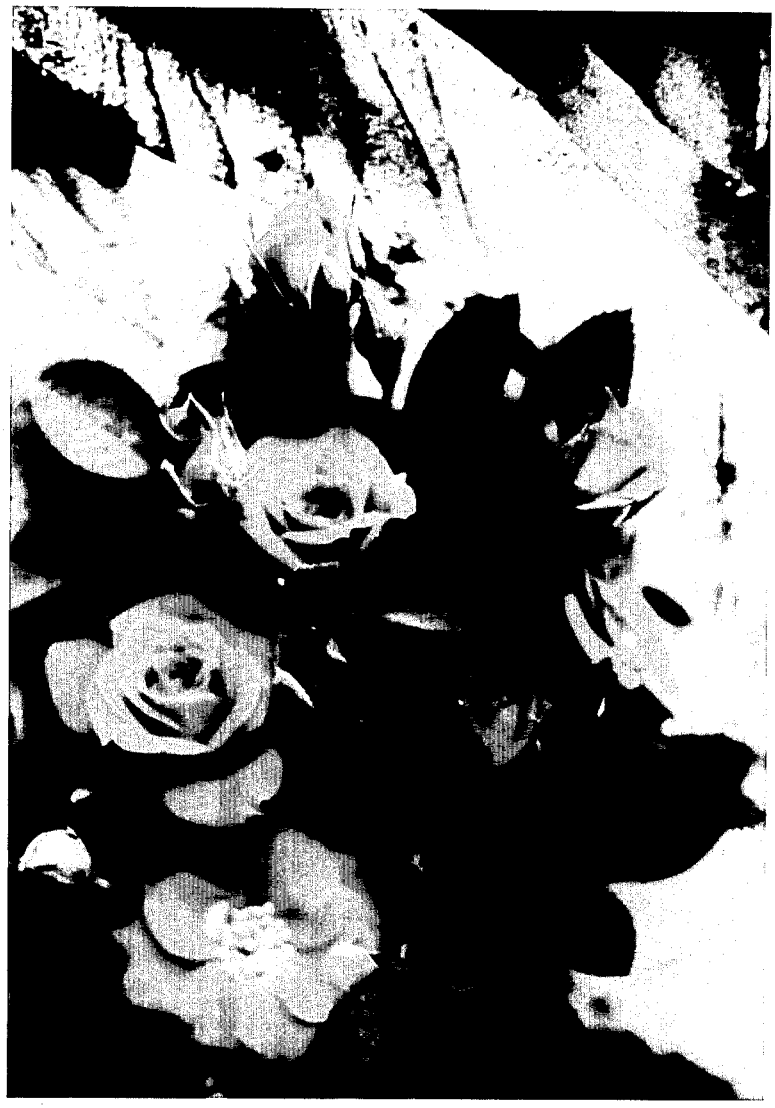

* * * * *